(12) United States Patent
Stangelmayer et al.

(10) Patent No.: US 9,016,573 B2
(45) Date of Patent: Apr. 28, 2015

(54) SENSOR UNIT AND MEASUREMENT METHOD

(75) Inventors: Achim Stangelmayer, Neuburg (DE); Damian Andrzejewski, Sinzing (DE)

(73) Assignee: PreSens—Precision Sensing GmbH, Regensburg (DE)

( * ) Notice: Subject to any disclaimer, the term of this patent is extended or adjusted under 35 U.S.C. 154(b) by 409 days.

(21) Appl. No.: 13/471,917

(22) Filed: May 15, 2012

(65) Prior Publication Data

US 2012/0291515 A1 Nov. 22, 2012

Related U.S. Application Data

(60) Provisional application No. 61/519,070, filed on May 16, 2011.

(30) Foreign Application Priority Data

May 16, 2011  (DE) .......................... 10 2011 050 389

(51) Int. Cl.
*G06K 7/10* (2006.01)
*G06T 7/40* (2006.01)

(52) U.S. Cl.
CPC ........................ *G06T 7/40* (2013.01)

(58) Field of Classification Search
USPC ..................... 235/454, 462.13, 375
See application file for complete search history.

(56) References Cited

U.S. PATENT DOCUMENTS

| | | |
|---|---|---|
| 3,961,530 A | 6/1976 | Helgesson |
| 4,907,037 A | 3/1990 | Boisde et al. |
| 5,828,058 A | 10/1998 | Yamada |
| 6,373,786 B1 | 4/2002 | Kagan et al. |
| 7,229,023 B2 | 6/2007 | Raskar |
| 7,606,451 B2 | 10/2009 | Morita |

(Continued)

FOREIGN PATENT DOCUMENTS

| | | |
|---|---|---|
| DE | 24 51 502 | 5/1975 |
| DE | 24 34 178 A1 | 1/1976 |

(Continued)

OTHER PUBLICATIONS

Luminescence Lifetime Imaging of Oxygen, pH, and Carbon Dioxide Distribution Using Optical Sensors by G. Liebsch, I, Klimant, B. Frank, G. Hoist, and O. S. Wolfbeis in Applied Spectroscopy 54, No. 4 (2000), pp. 548 to 559.

*Primary Examiner* — Allyson Trail
(74) *Attorney, Agent, or Firm* — Davidson, Davidson & Kappel, LLC

(57) ABSTRACT

A sensor unit is disclosed which includes a sensor and an information module. The sensor exhibits an optical behavior dependent on at least one variable of a sample. Sensor related information can be emitted by the information module as optical radiation. In embodiments the sensor related information includes calibration data for the sensor. The sensor related information may additionally include identification data for the sensor. In embodiments the information module measures at least one ambient parameter, and emits the measurement value in an optical signal. The measurement value is taken into account when determining at least one variable of a sample by means of the sensor unit. In embodiments the information module may also transmit status information of the sensor unit. Furthermore a method for determining a variable of a sample with a sensor unit and a measurement system is disclosed.

31 Claims, 2 Drawing Sheets

(56) References Cited

U.S. PATENT DOCUMENTS

| | | | |
|---|---|---|---|
| 7,616,315 B2 | 11/2009 | Sharrock et al. | |
| 7,819,328 B2 | 10/2010 | Levinson | |
| 8,297,513 B2 * | 10/2012 | Wallace et al. | 235/487 |
| 2007/0029388 A1 * | 2/2007 | Liu | 235/462.13 |
| 2008/0246969 A1 * | 10/2008 | Imura | 356/445 |
| 2009/0180513 A1 * | 7/2009 | Schick et al. | 374/44 |
| 2012/0187000 A1 * | 7/2012 | Kahn et al. | 205/782 |

FOREIGN PATENT DOCUMENTS

| | | |
|---|---|---|
| DE | 41 30 584 | 3/1993 |
| DE | 38 89 757 T2 | 12/1994 |
| DE | 692 24 281 | 10/1998 |
| DE | 690 32 351 | 12/1998 |
| DE | 201 07 116 U1 | 8/2001 |
| DE | 102 12 060 | 11/2003 |
| DE | 102 41 241 B4 | 8/2004 |
| DE | 10 2004 027 132 A1 | 1/2005 |
| DE | 600 16 440 | 12/2005 |
| DE | 10 2005 049 508 A1 | 10/2006 |
| DE | 10 2005 033 926 A1 | 1/2007 |
| DE | 10 2010 019 034 | 11/2011 |
| EP | 0 484 578 | 5/1998 |
| EP | 1 158 292 A2 | 11/2001 |
| EP | 1 712 896 B1 | 3/2010 |
| WO | WO9304403 | 3/1993 |
| WO | WO 01/55952 A2 | 8/2001 |
| WO | WO 2004/023421 A1 | 3/2004 |
| WO | WO 2004/048937 A2 | 6/2004 |

* cited by examiner

SENSOR UNIT AND MEASUREMENT METHOD

This claims the benefit of German Patent Application No. 10 2011 050 389.7, filed May 16, 2011 and of U.S. Provisional Patent Application No. 61/519,070 filed May 16, 2011, both applications are hereby incorporated by reference herein.

FIELD OF THE INVENTION

The present invention relates to a sensor unit with a sensor for determining at least one variable of a sample and to a method for determining at least one variable of a sample by means of a sensor of a sensor unit. In particular the invention relates to a sensor unit with a sensor which exhibits an optical behavior that depends on the at least one variable, and the method relates to such a sensor unit.

BACKGROUND

The article "Luminescence Lifetime Imaging of Oxygen, pH, and Carbon Dioxide Distribution Using Optical Sensors" by G. Liebsch, I. Klimant, B. Frank, G. Holst, and O. S. Wolfbeis in Applied Spectroscopy 54, Number 4 (2000), pages 548 to 559, describes the determination of various variables for samples in the wells of a microtitre plate via the dependence of the luminescence lifetime of substances used as sensors on the respective variable. It is not the luminescence lifetime itself which is determined, but a parameter depending on the luminescence behavior, wherein the parameter is calibrated against the variable to be determined.

U.S. Pat. No. 7,819,328 B2 relates to an optical identification element. This is assigned to an object and contains stored information on the object. The optical identification element includes an optical device which converts light incident from a reader into electrical energy. This energy is used for optical transmission of the information stored in the optical identification element to the reader. The stored information may for example be a retail price, counterfeit protection features, or sales restrictions.

U.S. Pat. No. 7,606,451 B2 discloses a communication system with at least one optical identification element and at least one optical reader. Between the reader and the identification element identification information is transmitted via light. The optical identification element has storing units for storing identification information, reflecting units for reflecting incident light, and modulating units for modulating the reflected light according to the stored identification information. Furthermore photoelectric converters are provided to supply the identification element with electrical energy from the incident light.

U.S. Pat. No. 7,229,023 B2 relates to an identification element with a transceiver for optical radiation and a transceiver for radio waves. The transceivers can be operated in different modes depending on the use of the identification element.

Optical methods for determining a variable by means of a sensor exhibiting an optical behavior depending on the variable are well known, the article cited above contains some, but in no way exhaustive, examples. In the article the sensors used are luminescence sensors, i.e. a respective sensor responds to an optical excitation with a luminescence phenomenon. In this application optical excitation means excitation with optical radiation, i.e. with electromagnetic radiation from the infrared to the ultraviolet spectral range; for this radiation here also the term light is used.

More generally speaking for the determination of a variable a sensor cooperates with optical radiation, and exhibits an optical behavior which depends on the variable. The optical radiation may for example impinge on the sensor as single light pulses, in series of light pulses, or as continuous illumination. A considerable advantage of such optical methods is that they are contactless methods, which for example may be carried out through a wall of a sample container which is transparent for the optical radiation used. Therein the sensor is in the sample container in contact with the sample; no electrical connections, which may be perturbing for some experiments, to the sensor are required. Such sensors also can easily be used with sterile containers; the sensors are put into the container before sterilisation, and are sterilised with the container. This greatly simplifies handling. Furthermore such sensors can be manufactured in relatively small a size; typically they have a diameter of about 5 mm and a thickness between 0.2 mm and 5 mm, there are also known examples of only 1 mm diameter. They therefore are considerably smaller than embodiments for example of commercial temperature sensors, like Pt100, which reach lengths of 3 cm and sometimes more, and which furthermore require electrical contacts.

SUMMARY OF THE INVENTION

Sensors of the kind mentioned can be used for the determination of any variable for which there are substances which show an optical behavior, for example a luminescence phenomenon or a color change, which depends on the variable, in response to an optical excitation. Examples of such variables are the partial pressure of gases, like oxygen or carbon dioxide, the concentration of substances or ions, the pH-value, temperature or pressure.

In any case such a sensor, prior to its use in a measurement for determining at least one variable, needs to be calibrated against the at least one variable. This may be done immediately before the sensor is used for a measurement, which, however, implies considerable effort. The sensors may also be calibrated by the manufacturer, and corresponding calibration data may be given to the customer by the manufacturer along with the sensor. For moderate precision requirements it may be sufficient to use a single set of calibration data for all sensors of a production batch. For higher precision requirements a separate set of calibration data is required for each sensor. The customer needs to adjust his measurement system according to the calibration data prior to using a sensor for a measurement. This, too, implies a certain effort for the customer.

A set of calibration data includes a number of data points which represent a relation between a quantity obtained by meteorological means from a sensor response of the respective sensor and the variable to be determined. Examples of a quantity obtained by meteorological means from a sensor response are the intensity of a luminescence response of the sensor, a phase difference between a time modulated excitation signal directed at the sensor and the corresponding time modulated response of the sensor, or a quantity obtained from integrals of the sensor response over time, like for example in the ratiometric method of the article cited above. Depending on the kind of variable a different number of data points is required for calibration. For example, for oxygen determination typically two data points are sufficient for calibration, for a pH-determination usually three or four data points are used for calibration. As the response of a sensor often also depends on the temperature in the environment in which the sensor is used, the calibration data points usually are valid only for one particular temperature. If measurements are to be carried out at various temperatures with high precision, a higher number of calibration data points is required, which correspond to different temperatures. Furthermore the calibration data points may be supplemented by specifying values for the slope and/or curvature of a curve interpolating the calibration data points, in order to define such a curve more precisely. The dependence of the calibration on a temperature or on further ambient parameters may be specified by parameters which express the dependence of the calibration data points on the ambient parameters instead of or in addition to further calibration data points, too. The effort due to calibration increases for the customer.

Apart from calibration also further aspects have to be taken into account in using a sensor. For example, the sensors usually only have a limited lifetime, i.e. they can only be used for reliable measurements during a limited period of time. Therefore it is necessary for a user to check a sensor with respect to its lifetime prior to using the sensor in a measurement. This implies an additional effort for the user and if neglected may lead to erroneous measurements.

It is an object of the invention to configure a sensor unit with a sensor which shows an optical behavior depending on at least one variable of a sample in such a way that the effort of a user of the sensor when using the sensor for a reliable determination of the at least one variable of the sample is reduced.

The present invention provides a sensor unit for determining at least one variable of a sample, wherein the sensor exhibits an optical behavior which depends on the at least one variable, comprising: an information module which is located on the sensor unit, and which is configured to emit sensor related information as optical radiation.

It is a further alternate or additional object of the invention to provide a method for determining at least one variable of a sample with a sensor which shows an optical behavior that depends on the at least one variable, in which the effort for a user of the sensor when using the sensor for a reliable determination of the at least one variable of the sample is reduced.

The present invention also provides a method for determining at least one variable of a sample from an optical behavior of a sensor of at least one sensor unit, wherein the optical behavior depends on the at least one variable, comprising the following steps:
a) emitting an optical signal onto an information module of the at least one sensor unit;
b) detecting an optical response signal generated by the information module, the optical response signal containing sensor related data stored in the information module;
c) determining the sensor related data from the optical response signal; and
d) determining the at least one variable from the optical behavior of the respective sensor taking into account the sensor related data determined in step c.

The sensor unit according to the invention includes a sensor for the determination of at least one variable of the sample. The sensor therein exhibits an optical behavior dependent on the at least one variable of the sample. According to the invention an information module configured to emit sensor-related information as optical radiation is provided on the sensor unit.

Advantageously the information module therein at least has a receiver unit for optical radiation, a data processing unit, and an emitter unit for the emission of sensor related information as optical radiation. Due to the receiver unit the information module is capable of receiving optical radiation, and thus also of receiving information as this optical radiation. Thus the information module can exchange information with its environment bidirectionally, i.e. it can both emit and receive information.

In preferred embodiments the sensor related information includes calibration data of the sensor. The calibration data are stored in the information module. In embodiments of the sensor unit with a data processing unit the calibration data are preferentially stored in the data processing unit, which then also controls the emission of the information. The emission of the information may be triggered by the information module receiving an optical signal. It is also conceivable to control the information module via optical signals transmitted to it, for example to put it into one of plural operation modes.

Advantageously the information stored in the information module and emittable by it includes, apart from the calibration data, identification data of the sensor. These for example include indications like a type specification of the sensor, a date of manufacture of the sensor, an indication until what date the sensor is usable, i.e. an expiry date, or an individual tag, for example a serial number of the sensor. It is conceivable that in dependence on the kind of an optical signal received by the information module, by corresponding control of the information module, which in preferred embodiments is accomplished by a data processing unit of the information module, either identification data or calibration data are emitted by the information module. Herein it is of course also conceivable, again in dependence on an optical signal received by the information module, to emit only a specific portion of the identification data or of the calibration data by the information module.

An optical behavior of a sensor may, apart from the at least one variable of a sample for the determination of which the optical behavior is exploited, also depend on at least one ambient parameter of the sensor unit, for example a temperature or a pressure. It therefore is advantageous if for such a sensor at least one corresponding ambient parameter is measured by a device in the information module, and if the corresponding measurement value of the at least one ambient parameter is emitted by the information module as optical radiation. This can be done close in time with the capturing of the optical behavior of the sensor, and also localised at the sensor unit. Close in time here means within a distance in time from capturing the optical behavior which is small compared with relevant time scales in the sample investigated, i.e. small compared with the time scales of the processes studied in the sample. As the determination of the at least one ambient parameter is done also localised at the sensor unit, as the information module is a part of the sensor unit, a value of the at least one ambient parameter results which corresponds in time and space more reliably to the capturing of the optical behavior than if the at least one ambient parameter were measured with a separate sensor. Also there is no effort for this separate sensor and no additional perturbation of the investigated sample by this separate sensor. Due to the additional emission of the measurement value of the at least one ambient parameter in an optical signal this measurement value can be taken into account in the determination of the at least one variable from the optical behavior of the sensor.

In an advantageous further development of the sensor unit according to the invention the information module is configured to emit an optical signal if a measurement value is found at measuring the at least one ambient parameter which is outside of a pre-defined admissible range, stored in the information module, for the respective ambient parameter. The optical signal then contains information on the crossing of a limit of the admissible range or directly indicates this crossing. A limit of the admissible range here is a value of the respective ambient parameter which corresponds to a boundary of the admissible range. Usually an admissible range has an upper and a lower boundary or either only an upper or a lower boundary.

The sensors, or more precisely the sensor substances used for the sensors, largely show the phenomenon of bleaching, i.e. the sensor substances are slowly destroyed by the repeated illumination with light pulses or the continuous exposure to light over longer periods of time, the sensors thus lose or at least change their optical behavior depending on the at least one variable. In the case of a luminescence sensor this for example means that, if the sensor already has received a plurality of light pulses for the excitation of a luminescence, the intensity of a luminescence response to a given excitation light pulse is lower than in the case of a new sensor which has not yet received any previous excitation light pulses. The effect of bleaching can to a certain degree be countered by a recalibration, so that the changed optical behavior of the sensor is taken into account; eventually, however, the sensor becomes unfit for use and needs to be replaced.

In advantageous embodiments of the sensor unit according to the invention the information module therefore is configured to count light pulses incident on the sensor which are emitted onto the sensor for the determination of the at least one variable. The information module for example may emit the current count of light pulses in an optical signal, for example in response to a control signal received by the information module. An alternative or additional possibility is for the information module to store the number of light pulses received, and autonomously to emit an optical signal if a pre-defined limit for this number is crossed, in order to indicate the necessity of a recalibration or the unfitness for use of the sensor directly or in order to emit corresponding information. In the latter case the optical signal may for example be information for a measurement system used for the determination of the at least one variable, which in response to the optical signal outputs a corresponding notification to a user; in the first case the optical signal may be a light signal that can be directly perceived by the user. The pre-defined number of light pulses, i.e. the limit, therein advantageously is stored in the information module.

In a further advantageous embodiment the information module is configured to determine the total light exposure of the sensor, i.e. the total of the light energy which has impinged on the sensor; this includes the light energy incident as light pulses when determining at least one variable, and the light energy from exposure of the sensor to ambient light. It is possible that herein in embodiments only that light energy is registered which belongs to a particular range of the optical spectrum, i.e. a particular wavelength range. Advantageously this is the range causing bleaching of the sensor. If the total light exposure crosses a pre-defined limit, the information module emits an optical signal containing corresponding warning information or indicating the crossing of the limit as a light signal directly perceivable by a user. This embodiment is for example particularly suitable to indicate sensors which have become unusable by inadequate storing without light protection. If a sensor for instance is stored in daylight without protection, and thus becomes unusable, the information module can emit an optical signal, for example a continuous signal or an intermittent signal, in order to enable a user to identify the unusable sensor easily. The energy for the emission of this signal may advantageously be taken from the light incident on the information module. The predefined limit therein is advantageously stored in the information module.

In some fields of application a precise operation of the sensor is of extraordinary importance. This is in particular the case for the use of the sensor in examinations in the field of medicine, as here human lives may depend on the fact that variables are determined with the sensor correctly. In particular, but not exclusively, for such examinations in embodiments of the sensor unit the information module may be configured to put the sensor unit into a state unfit for measuring, if the number of the light pulses directed onto the sensor unit and/or the total light exposure of the sensor, and/or a measurement value of at least one ambient parameter of the sensor unit crosses a predefined limit. The information module may for example achieve the unfitness for measurement by the emitter unit, upon incidence of a light pulse on the sensor unit, emitting an optical signal which perturbs the capturing of the optical behavior of the sensor. In this way a determination of a variable, i.e. a measurement, with the sensor is impossible, and drawing wrong conclusions from unreliable measurements is avoided.

Advantageously the sensor unit is sterilizable. This on the one hand is an important prerequisite in order not to contaminate a sample by micro-organisms on the sensor unit, on the other hand also simplifies handling the sensor unit. The sensor unit may be placed into a sample container and sterilised with the sample container. In this way it is in particular possible to provide a user with a sterile and sealed sample container containing a sensor unit.

Sterilisation may be done by thermal or chemical methods or also by exposition of the sensor unit, as the case may be together with a sample container, to UV light, nuclear radiation, i.e. alpha, beta, or gamma rays, or artificially generated electron rays. Sensor unit and also sample container may in particular also be sterilizable in an autoclave. In any case the sensor unit needs to be configured in such a way that its operation is not adversely affected by the sterilisation method. In comparison with prior art sensors new issues arise for sensor units according to the invention due to the information module. This, usually an electronic element, needs to be such that it passes the sterilisation process undamaged.

The sensor unit may have an energy supply of its own. In a particularly preferred embodiment, however, the sensor unit is configured to take the energy required for operation of the information module from optical radiation. In particular the information module may be configured in such a way that it absorbs part of the light directed onto the sensor unit for the determination of the at least one variable and converts this light into electrical energy. The sensor unit in embodiments may have an energy storage. Advantageously the sensor unit is in particular configured to store energy taken from optical radiation in the energy storage.

In embodiments the receiver unit includes at least one photo detector. This for example may be a photo diode. The emitter unit in embodiments includes at least one light source; advantageously an LED (light emitting diode) may be used here. In some embodiments a common optoelectronic element corresponds to emitter and receiver unit, which can both emit optical radiation and receive optical radiation. Therein moreover a switch element is provided, by which the optoelectronic element can be switched between an emitting state, in which it emits optical radiation, and a receiving state, in which it can receive optical radiation.

In embodiments the information module is an optoelectronic semiconductor chip. The semiconductor chip therein may be attached to a sensor, and thus form a sensor unit according to the invention together with the sensor. As such optoelectronic semiconductor chips can be manufactured in sizes of 1 mm diameter or even less, such a semiconductor chip implies no relevant additional perturbation of a sample beyond the, usually also small, perturbation by the sensor.

Alternatively it is also possible to provide the sensor on a carrier, and to form the information module in the carrier; the carrier may be a semiconductor substrate.

In embodiments of the sensor unit according to the invention the optical behavior of the sensor is a luminescence phenomenon. The sensor thus exhibits a substance which can be excited to show luminescence by optical radiation. The luminescence phenomenon therein depends on at least one variable for the determination of which for a sample the sensor is used. The dependence may for example comprise that the luminescence phenomenon, in dependence on the at least one variable, occurs with different intensity for a given excitation intensity, or may comprise that the wavelength region of the luminescence depends on the at least one variable. With particular preference, however, a dependence of the decay time of the luminescence on the at least one variable is exploited.

In different embodiments of the sensor unit according to the invention the optical behavior is a dependence of a color of the sensor on the at least one variable. For capturing it the sensor may be illuminated with light of a defined spectral composition, and the light scattered back from the sensor may be analysed with respect to its color. This for example may be done by determining the spectral composition of the light scattered back, by an analysis of the light scattered back by means of one or plural filters, or by further known methods of color measurement.

In yet further different embodiments the optical behavior of the sensor comprises a change of the reflection and/or absorption properties of the sensor for optical radiation in dependence on the at least one variable. The reflection/absorption properties can for example be determined by illumination of the sensor with light of defined spectral composition and intensity, and analysis of the light reflected by the sensor or transmitted through the sensor, respectively. Therein in particular the intensity and/or the spectral composition of the reflected or transmitted light may be determined.

In some embodiments the sensor is configured to cooperate with light from a first wavelength region for the determination of the at least one variable. Therein the information module is configured to emit and receive light from a second wavelength region. Herein the first wavelength region and the second wavelength region do not overlap. This may for example be advantageously exploited by choosing the second wavelength region in such a way that light from this wavelength region does not bleach the sensor. In this way optical signals for information interchange with the information module do not adversely affect the lifetime of the sensor. Furthermore it is possible to supply energy to the information module by optical radiation from the second wavelength region, without effecting a bleaching of the sensor.

In different embodiments the information module is configured to emit light with at least one first wavelength, and to receive light with at least one second wavelength, and the sensor is configured to cooperate, for the determination of the at least one variable, with light which comprises at least the first wavelength or at least the second wavelength.

In preferred embodiments the sensor unit operates with light in a wavelength region from 400 nm to 750 nm. Therein the sensor is configured to cooperate with light from the wavelength region between 400 nm and 750 nm for the determination of the at least one variable. Furthermore in these embodiments the information module is sensitive to light from this wavelength region, and the information module emits optical signals in this wavelength region.

The method according to the invention is for determining at least one variable of a sample. To this end an optical behavior of a sensor of at least one sensor unit is captured, wherein the optical behavior depends on the at least one variable, and the at least one variable is determined therefrom. In order to capture the optical behavior of the respective sensor the sensor unit is exposed to light. This can be achieved by explicit illumination of the sensor unit or by exposition of the sensor unit to ambient light.

According to the invention sensor related data of the respective sensor are read from an information module of the at least one sensor unit. Reading of sensor related data stored in the information module is done as follows: An optical signal is sent to the information module. In response, the information module emits an optical response signal, which contains the sensor related data. The response signal is detected and the sensor related data are determined from the response signal.

From the optical behavior of the respective sensor the at least one variable of the sample is found, wherein according to the invention the read sensor related data are taken into account. Advantageously the determination of the at least one variable of the sample and the taking into account of the read sensor related data are done automatically.

In embodiments of the method the sensor related data are read at least once for a respective sensor. The at least one variable can be determined plural times, for example in order to determine a behavior in time of the at least one variable. This implies that over a period of time the optical behavior of the respective sensor is captured repeatedly, and respectively the at least one variable is determined therefrom. Herein it is not necessary to read the sensor related data from the information module for each determination of the at least one variable.

In an advantageous further development of the method at least one ambient parameter of the sensor unit, for example a temperature or a pressure, is measured by the information module of the at least one sensor unit. The measurement value of the at least one ambient parameter is emitted by the information module as an optical signal. The optical signal is detected and evaluated with respect to the measurement value. The measurement value of the at least one ambient parameter is taken into account in the determination of the at least one variable.

For the determination of the at least one variable the at least one sensor unit is exposed to light which cooperates with the sensor of the at least one sensor unit for the determination of the at least one variable, as already mentioned. Part of this light impinges on the information module of the sensor unit. In an embodiment of the method the information module takes the energy required for its operation from this light, and buffers at least part of it in an energy storage. Once the optical behavior of the sensor has been captured, the information module emits an optical signal with a measurement value of the at least one ambient parameter. The energy required for this is taken from the energy storage. In this way the capturing of the optical behavior of the sensor is not perturbed by the optical signal from the information module. The at least one ambient parameter may be measured by the information module during or after the capturing of the optical behavior of the sensor.

In preferred embodiments the read sensor related data include calibration data of the sensor of the at least one sensor unit.

In embodiments of the method, prior to determining the at least one variable, a calibration of the sensor may be performed and the calibration data thereby found transmitted to the information module by an optical signal, to be stored there. This embodiment of the method is applicable both to recently manufactured sensors and to sensors which have been in use for some time and are to be recalibrated, so that they may be used reliably for the determination of the at least one variable in the future.

In an embodiment of the method the at least one variable is not determined from the optical behavior of the respective sensor, if the sensor related data indicate an unfitness for use of the respective sensor. In this way unreliable, because potentially erroneous, measurement results are avoided. Such an unfitness for use of the respective sensor may, dependent on the type of the respective sensor, for example result from the fact that the expiry date of the respective sensor has passed, that the respective sensor has already been exposed to a number of light pulses which is beyond a predefined limit advantageously stored in the information module, or that a total light exposure of the respective sensor is beyond a predefined limit advantageously stored in the information module. A further possibility resulting in an unfitness for use of the sensor is that the sensor has been exposed to inadmissible ambient conditions. The ambient conditions of the sensor may be determined by a device for determining at least one ambient parameter of the sensor unit.

BRIEF DESCRIPTION OF THE DRAWINGS

In what follows embodiments shall illustrate the invention and its advantages with reference to the accompanying figures. There is shown in FIG. 1 a schematic representation of the sensor unit.

DETAILED DESCRIPTION

Figure 1:
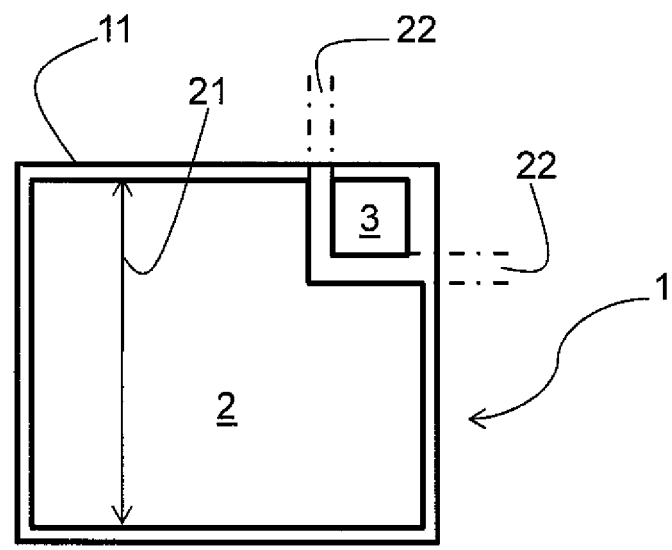

In the figures identical reference numerals are used for like elements or elements of like function. Furthermore, for the sake of clarity only those reference numerals are shown in a figure which are required for the description of the respective figure or for establishing the context of the figure with the other figures.

FIG. 1 shows a sensor unit 1 having a sensor 2 and an information module 3. Sensor 2 and information module 3 are provided on a carrier 11. As indicated in the figure, the information module 3 typically is small in comparison with the sensor 2, and thus does not imply a perturbation of a sample 7 (see FIG. 4) beyond the perturbation by the sensor 2 when determining a variable of the sample 7. The sensor 2 is formed by a sensor substance applied on the carrier 11, the sensor substance showing an optical behavior dependent on the at least one variable. The carrier 11 may for example be a film. It is in any case important that the sensor substance is reachable by light to which the sensor unit 1 is exposed for the determination of the at least one variable. Likewise light must be able to impinge on the information module 3. It is indicated in the figure that the information module 3 is spatially localised close to the sensor 2, here this means that distances 22 between the information module 3 and the sensor 2 are smaller than a width 21 of the sensor 2. This is advantageous, because then on the one hand the sensor unit 1 is compact, and on the other hand a possible measurement of at least one ambient parameter of the sensor unit 1 by the information module 3 is done at a position which differs from a position of the sensor 2 by less than the width 21 of the sensor 2. Within this spatial precision the measurement of the at least one ambient parameter by the information module 3 corresponds to a measurement of the at least one ambient parameter at the position of the sensor 2.

Figure 2:
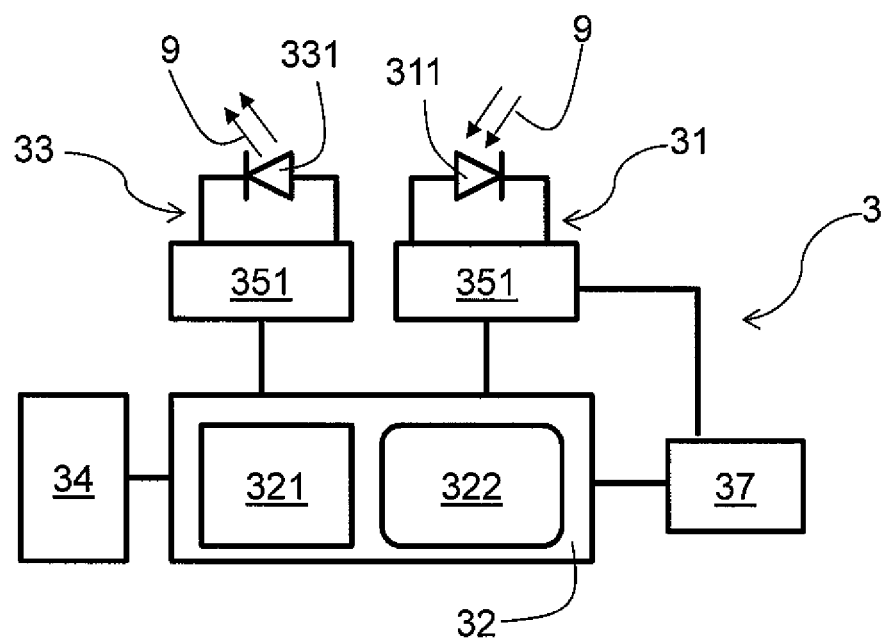
FIG. 2 a schematic representation of an embodiment of the information module.

FIG. 2 is a schematic representation of an information module 3. It includes a receiver unit 31 for optical radiation 9, a data processing unit 32, and an emitter unit 33 for optical radiation 9. Furthermore the embodiment shown exhibits a device 34 for measuring at least one ambient parameter of the sensor unit 1 (see FIG. 1) and an energy storage 37. In the embodiment shown the receiver unit 31 is a photodiode 311 with corresponding control electronics 351, the emitter unit 33 is an LED 331 with corresponding control electronics 351. Instead of the photodiode 311 a different suitable photodetector may be used, and instead of the LED 331 a different light source may be used. Adequate alternatives are known to a person skilled in the art. The data processing unit 32 includes a processor 321 and a memory 322. The processor 321 controls the information module 3 and performs the calculations required for the correct operation of the information module 3. For both purposes the processor 321 cooperates with the memory 322. The memory 322 may for example be an EEPROM.

The device 34 for measuring at least one ambient parameter determines the ambient parameter in a way known to a person skilled in the art; for example, a temperature may be measured resistively. Under control by the processor 321, a measurement value determined by the device 34 may for example first be stored in the memory 322, in order to be emitted as an optical signal by the emitter unit 33 at a later time.

In the embodiment shown the energy storage 37 is for buffering energy gained from optical radiation received by the receiver unit 31. Therein the received light is photoelectrically converted, and at least a part of the energy of the received light is buffered in the energy storage 37, for example capacitively or in a different way known to a person skilled in the art, in order to supply energy to the information module 3 according to need. For example energy is required for the emission of an optical signal by the emitter unit 33.

The receiver unit 311 is not only for providing energy to the information module 3, but also for receiving optical control signals. These are transmitted to the processor 321, which triggers corresponding steps. For example the processor 321, in dependence on the control signals received, may trigger the emission of particular information stored in the memory 322 by the emitter unit 33. This information may comprise measurement values of ambient parameters of the sensor unit 1 or sensor related data, like calibration data of the sensor 2 (see FIG. 1), or identification data of the sensor 2.

Figure 3:
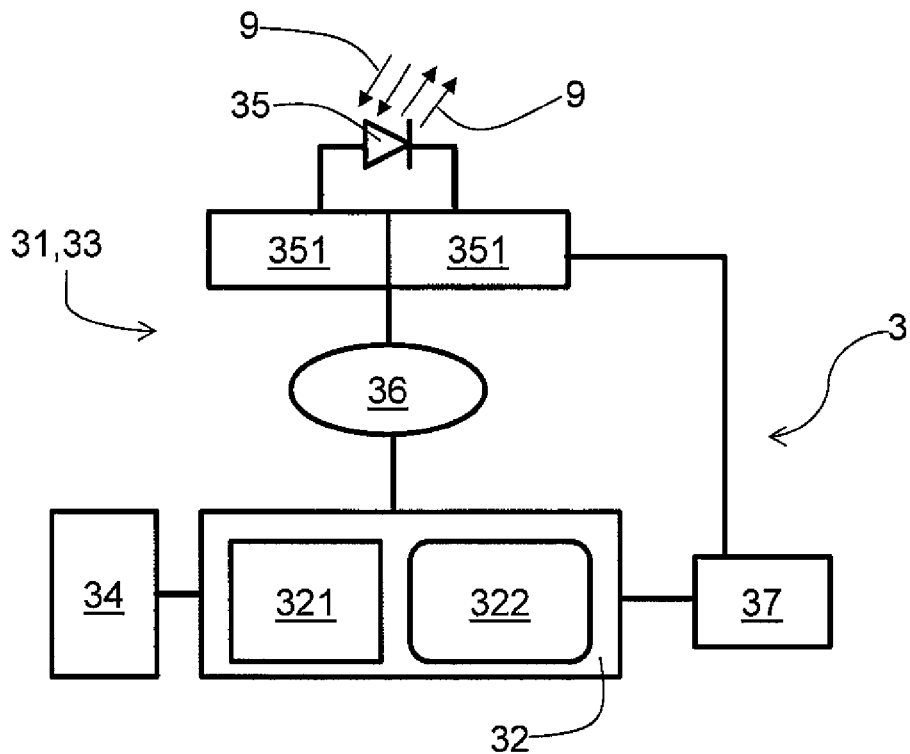
FIG. 3 a schematic representation of a further embodiment of the information module.

FIG. 3 is a schematic representation of a further embodiment of the information module 3. To the receiver unit 31 and the emitter unit 33 there corresponds a common optoelectronic element 35, which is able to both emit and receive optical radiation 9. Control electronics 351 is provided for the optoelectronic element 35. Furthermore a switch element 36 is provided, by which the optoelectronic element 35 can be switched between an emitting state and a receiving state. The further elements shown have already been discussed in the context of FIG. 2. The advantage of this embodiment in comparison with the embodiment of FIG. 2 is that here only one optoelectronic element 35 is used, contrary to two optoelectronic elements in the embodiment of FIG. 2, LED 331 and photodiode 311. In this way the space required for the information module 3 is reduced; this implies that an embodiment according to FIG. 3 can be built in a smaller size than an embodiment according to FIG. 2.

Figure 4:
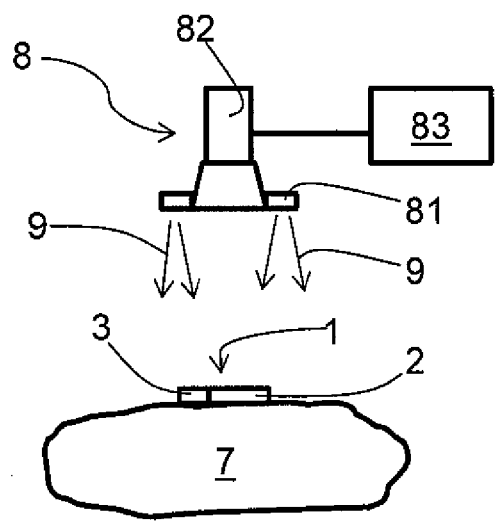
FIG. 4 a schematic representation of a measuring system with a sample and a sensor unit.

FIG. 4 schematically shows a measuring system 8 for the determination of at least one variable of a sample 7 in cooperation with a sensor unit 1 according to the invention, which includes an optical sensor 2, which in the embodiment shown is a luminescence sensor, and an information module 3. The measuring system 8 has a light source 81, which here is a ring light, a detection apparatus 82, and a control and evaluation unit 83. The detection apparatus 82 may for example be a camera with CCD chip. In the embodiment shown the sensor unit 1 is provided on the sample 7. It is, however, also possible to use the sensor unit in a liquid sample; for this purpose, the sensor unit 1 is put into a container which contains the liquid sample or is provided for receiving the liquid sample, and advantageously is fixed at an inner side of a wall of the container. The exchange of optical signals between measuring system 8 and sensor unit 1 then occurs through the wall of the container, which needs to be transparent for the wavelengths used for the optical signals. Of course, the measuring system 8 may also cooperate with a plurality of sensor units 1 according to the invention. Therein it is possible that the sensors 2 of at least two sensor units 1 differ with respect to the variable to which they are sensitive. From the above it is clear that in different embodiments the sensor 2 need not be a luminescence sensor, but that the optical behavior depending on the at least one variable of the sample 7 may for example be a change of the color of the sensor 2 depending on the at least one variable, or may comprise that the reflection and/or absorption properties of the sensor 2 depend on the at least one variable of the sample 7.

Under control by the control- and evaluation unit 83 the light source 81 emits optical radiation 9 onto the sensor unit 1; the optical radiation 9 therein reaches both the sensor 2 and the information module 3, as indicated by the diverging arrows. The optical radiation 9 therein may be used for exciting a luminescence of the sensor 2, for communication between measuring system 8 and information module 3, for providing energy to the information module 3, or for a combination of the stated possibilities. The communication between measuring system 8 and information module 3 is for the reading of sensor related data, for example calibration data, and, as the case may be, identification data of the sensor 2 by the measuring system 8; the data transmitted are processed in the control and evaluation unit 83.

Depending on the configuration of the information module 3 additional information may be transmitted to the measuring system 8 by the information module 3, for example a measurement value for at least one ambient parameter of the sensor unit 1 or status information of the sensor unit 1, for example alerts.

Furthermore control signals may be transmitted from the measuring system 8 to the information module 3 by the optical radiation 9. In this way the information module 3 may be put into different modes of operation, or particular information stored in the information module may be specifically requested. The different modes of operation of the information module 3 may for example comprise states of operation of the information module 3 which are adapted to specific measuring protocols and corresponding types of excitation of the sensor 2, for example particular pulse sequences or pulse durations of the light source 81. In this way, for example, a defined delay between an excitation light pulse for the sensor 2 and the emission of an optical signal with the measurement value of an ambient parameter by the information module 3 can be set, in order to emit the optical signal only after the detection of a luminescence response of the sensor 2 to an excitation light pulse has ended.

Likewise it is possible to transmit data to the information module 3 by optical radiation for storing for a later retrieval. This may for example be useful if the sensor 2 is recalibrated, for example in order to take into account a bleaching of the sensor 2. The calibration data determined by the recalibration are then transmitted to the information module 3 by optical radiation and there are stored. For future measurements first the modified calibration data are read from the information module 3. In this way the sensor unit may easily be used for the reliable determination of at least one variable of the sample 7 over a longer period of time than without recalibration. Storing the modified calibration data in the information module 3 makes a continued comfortable and easy use of the sensor 2 possible.

The invention has been described with reference to specific embodiments. However, that alterations and modifications are possible without leaving the scope of the subsequent claims.

What is claimed is:

1. A sensor unit comprising:
   a sensor for determining at least one variable of a sample, the sensor formed by a sensor substance exhibiting an optical behavior dependent on the at least one variable, the sensor substance applied on a carrier; and
   an information module configured to emit sensor related information as optical radiation the information module having a receiver for optical radiation, a date processing unit, and an emitter for emitting the sensor related information as optical radiation.

2. The sensor unit as recited in claim 1 wherein the sensor related information includes calibration data for the sensor stored in the information module.

3. The sensor unit as recited in claim 1 wherein the sensor related information includes identification data of the sensor, the identification data including at least one of the data types: type of sensor, date of manufacture, expiry data, individual tag of the sensor.

4. The sensor unit as recited in claim 1 wherein the information module has a measurer for measuring at least one ambient parameter of the sensor unit, the sensor related information including a measurement value of the at least one ambient parameter.

5. The sensor unit as recited in claim 4 wherein the information module is configured to emit, in the case of measuring a value of the at least one ambient parameter outside of a predefined admissible range stored in the information module, an optical signal containing information on a crossing of a limit of the admissible range or indicating the crossing directly.

6. The sensor unit as recited in claim 4 wherein the at least one ambient parameter is a temperature or a pressure.

7. The sensor unit as recited in claim 6 wherein the information module is configured to render the sensor unit unfit for measuring, if a limit is crossed.

8. The sensor unit as recited in claim 1 wherein the information module is configured to count light pulses incident on the sensor which are required for determining at least one variable, and to emit information on the count as an optical signal and/or to emit an optical signal if a limit is crossed, the optical signal directly indicating the need for a recalibration or the unfitness for use of the sensor, or containing information thereon.

9. The sensor unit as recited in claim 1 wherein the information module is configured to determine the total light exposure of the sensor within at least one wavelength region, and to emit an optical signal if a limit is crossed, wherein the signal contains a corresponding warning or directly indicates the crossing of the limit.

10. The sensor unit as recited in claim 1 wherein the sensor unit is sterilizable by a thermal or chemical method or by exposure to at least one of the following kinds of radiation: UV light, nuclear radiation, electron rays.

11. The sensor unit as recited in claim 10 wherein the sensor unit is autoclavable.

12. The sensor unit as recited in claim 1 wherein the sensor unit is configured to take the energy required for operation of the information module from optical radiation.

13. The sensor unit as recited in claim 1 wherein the sensor unit has an energy storage.

14. The sensor unit as recited in claim 13 wherein the sensor unit is configured to store energy taken by it from optical radiation in the energy storage.

15. The sensor unit as recited in claim 1 wherein the receiver has at least one photo detector.

16. The sensor unit as recited in claim 1 wherein the emitter has at least one light source.

17. The sensor unit as recited in claim 1 wherein the receiver and the emitter form a common optoelectronic element, and further comprising a switch switching the optoelectronic element between an emitting state and a receiving state.

18. The sensor unit as recited in claim 1 wherein the information module is an optoelectronic semiconductor chip.

19. The sensor unit as recited in claim 1 wherein the optical behavior of the sensor is a luminescence phenomenon.

20. The sensor unit as recited in claim 1 wherein the optical behavior of the sensor is a change of the reflection and/or absorption properties for optical radiation of the sensor or a change of color of the sensor.

21. The sensor unit as recited in claim 1 wherein the sensor is configured to cooperate with light from a first wavelength region for determining the at least one variable, and the information module is configured to emit and to receive light from a second wavelength region wherein the first wavelength region and the second wavelength region do not overlap.

22. The sensor unit as recited in claim 1 wherein the information module is configured to emit light of at least one first wavelength, and to receive light of at least one second wavelength, and wherein the sensor is configured, for determining the at least one variable, to cooperate with light which comprises at least the first wavelength or at least the second wavelength.

23. The sensor unit as recited in claim 1 wherein the sensor is configured, for determining the at least one variable, to cooperate with light of the wavelength region between 400 nm and 750 nm, the information module is sensitive for light from this wavelength region, and light from this wavelength region can be emitted by the information module.

24. A method for determining at least one variable of a sample from an optical behavior of a sensor of at least one sensor unit wherein the optical behavior depends on the at least one variable, the method comprising the following steps:
   a) emitting an optical signal onto an information module of the at least one sensor unit;
   b) detecting an optical response signal generated by the information module, the optical response signal containing sensor related data stored in the information module;
   c) determining the sensor related data from the optical response signal; and
   d) determining the at least one variable from the optical behavior of the respective sensor taking into account the sensor related data determined in step c.

25. The method as recited in claim 24 wherein step d is carried out repeatedly, without reading the sensor related data stored in the information module repeatedly from the information module.

26. The method as recited in claim 24 wherein in addition to the detection of an optical behavior of a respective sensor
   at least one ambient parameter of the at least one sensor unit is measured by the information module of the at least one sensor unit,
   the measurement value of the at least one ambient parameter is emitted as an optical signal by the information module,
   the optical signal is detected and the measurement value of the at least one ambient parameter is determined from the optical signal, and
   the measurement value of the at least one ambient parameter is taken into account in the determination of the at least one variable.

27. The method as recited in claim 26 wherein the energy required for operation of the information module is taken from a part of the light to which the sensor unit is exposed so that the light cooperates with the respective sensor for the determination of the at least one variable, this energy is buffered in an energy storage, and the optical signal is emitted by the information module after capturing the optical behavior of the respective sensor is complete.

28. The method as recited in claim 24 wherein the sensor related data include at least calibration data of the sensor of the at least one sensor unit.

29. The method as recited in claim 28 wherein prior to the determination of the at least one variable a calibration of the sensor is done, and the calibration data determined in this way are transferred to the information module by an optical signal and are stored there.

30. The method as recited in claim 24 wherein the at least one variable is not determined from the optical behavior of the respective sensor, if the respective sensor is found from the sensor related data to be unusable.

31. A sensor unit comprising:
   a sensor for determining at least one variable of a sample, the sensor exhibiting an optical behavior dependent on the at least one variable; and
   an information module configured to emit sensor related information as optical radiation,
   wherein the information module is configured to determine the total light exposure of the sensor within at least one wavelength region, and to emit an optical signal if a limit is crossed, wherein the signal contains a corresponding warning or directly indicates the crossing of the limit.

* * * * *